(12) United States Patent
Seely-Morgan

(10) Patent No.: US 11,547,517 B2
(45) Date of Patent: Jan. 10, 2023

(54) DEVICES FOR SUPPORTING A MEDICAL INSTRUMENT AND METHODS OF USE

(71) Applicant: Melissa Seely-Morgan, Dunwoody, GA (US)

(72) Inventor: Melissa Seely-Morgan, Dunwoody, GA (US)

( * ) Notice: Subject to any disclaimer, the term of this patent is extended or adjusted under 35 U.S.C. 154(b) by 0 days.

(21) Appl. No.: 17/397,273

(22) Filed: Aug. 9, 2021

(65) Prior Publication Data

US 2021/0393362 A1 Dec. 23, 2021

Related U.S. Application Data

(62) Division of application No. 16/308,068, filed as application No. PCT/US2018/043448 on Jul. 24, 2018, now Pat. No. 11,109,933.

(Continued)

(51) Int. Cl.
*A61B 50/20* (2016.01)
*F16B 2/00* (2006.01)
*F16M 11/04* (2006.01)
*F16M 11/40* (2006.01)
*A61B 50/00* (2016.01)

(52) U.S. Cl.
CPC .............. *A61B 50/20* (2016.02); *F16B 2/005* (2013.01); *F16M 11/041* (2013.01); *F16M 11/40* (2013.01); *A61B 2050/002* (2016.02)

(58) Field of Classification Search
CPC ....... A61B 50/20; F16B 2/005; F16M 11/041; F16M 11/40
USPC ... 248/160, 440, 440.1, 316.1, 316.6, 316.7, 248/121, 122.1, 124.1, 124.2, 229.16, 248/229.26, 228.7, 230.7, 231.81
See application file for complete search history.

(56) References Cited

U.S. PATENT DOCUMENTS

| | | | |
|---|---|---|---|
| 2,510,198 A | 6/1950 | Tesmer | |
| 3,402,442 A | 9/1968 | Kruger | |

(Continued)

FOREIGN PATENT DOCUMENTS

| | | |
|---|---|---|
| DE | 19808220 | 2/1998 |
| WO | 2010084322 | 7/2010 |

OTHER PUBLICATIONS

International Search Report and Written Opinion dated Sep. 25, 2018, from International Application No. PCT/US2018/043448, 10 pages.

(Continued)

*Primary Examiner* — Terrell L McKinnon
*Assistant Examiner* — Michael McDuffie
(74) *Attorney, Agent, or Firm* — Meunier Carlin & Curfman LLC

(57) ABSTRACT

Various implementations include a device for holding and supporting a medical instrument in a position. For example, the medical instrument may include a percutaneous procedure apparatus, such as a needle (e.g., biopsy needle, anesthesia needle) or needle holder. In some implementations, the device holds and supports the percutaneous procedure apparatus and liberates the procedure operator's hands from direct beam exposure, which lowers the risk of complications and radiation exposure to patients and procedure operators. The device also increases the effectiveness of the procedure by holding and supporting the apparatus in the intended position.

21 Claims, 17 Drawing Sheets

Related U.S. Application Data

(60) Provisional application No. 62/650,249, filed on Mar. 29, 2018, provisional application No. 62/649,920, filed on Mar. 29, 2018.

(56) References Cited

U.S. PATENT DOCUMENTS

| | | | |
|---|---|---|---|
| 3,858,578 A | 1/1975 | Milo | |
| 4,573,452 A | 3/1986 | Greenberg | |
| 4,813,107 A | 3/1989 | Cetrone | |
| 4,883,053 A | 11/1989 | Simon | |
| 5,103,384 A | 4/1992 | Drohan | |
| 5,276,596 A | 1/1994 | Krenzel | |
| 5,381,989 A | 1/1995 | Jackson | |
| 5,489,075 A | 2/1996 | Ible | |
| 5,513,827 A | 5/1996 | Michaelson | |
| 5,636,815 A * | 6/1997 | Wilson | F16M 11/28 248/219.2 |
| 5,765,820 A | 6/1998 | Marusiak | |
| 5,823,658 A | 10/1998 | Doddy | |
| 5,842,670 A | 12/1998 | Nigoghosian | |
| 5,937,537 A | 8/1999 | Miller | |
| 5,944,696 A | 8/1999 | Bayless | |
| 6,249,713 B1 | 6/2001 | Geiger et al. | |
| 6,390,424 B1 | 5/2002 | Kidushim | |
| 6,520,495 B1 | 2/2003 | La Mendola | |
| 6,688,564 B2 | 2/2004 | Salvermoser | |
| 6,983,930 B1 | 1/2006 | La Mendola | |
| 7,466,303 B2 | 12/2008 | Yi et al. | |
| 7,766,313 B2 | 8/2010 | Panosian | |
| 7,824,417 B2 | 11/2010 | Magnusson et al. | |
| 8,272,612 B2 | 9/2012 | Thorpe | |
| 8,603,078 B2 | 12/2013 | Stefanchik et al. | |
| 8,613,748 B2 | 12/2013 | Velusamy et al. | |
| 8,727,290 B1 | 5/2014 | De La Matta | |
| 9,408,627 B2 | 8/2016 | Sahni | |
| 10,512,322 B2 | 12/2019 | Washington | |
| 11,109,933 B2 * | 9/2021 | Seely-Morgan | A61B 50/20 |
| 11,241,072 B2 * | 2/2022 | LaPoint | F16M 11/08 |
| 2002/0087166 A1 | 7/2002 | Brock et al. | |
| 2004/0089778 A1 | 5/2004 | Valentine | |
| 2004/0211868 A1 | 10/2004 | Holmes | |
| 2004/0243146 A1 | 12/2004 | Chesbrough et al. | |
| 2004/0260312 A1 | 12/2004 | Magnusson et al. | |
| 2005/0092877 A1 | 5/2005 | Carnevali | |
| 2006/0086571 A1 | 4/2006 | Hubble | |
| 2006/0259018 A1 | 11/2006 | Shilkrut | |
| 2008/0006551 A1 | 1/2008 | Tolley et al. | |
| 2011/0028797 A1 | 2/2011 | Yee et al. | |
| 2012/0022368 A1 | 1/2012 | Brabrand et al. | |
| 2012/0178337 A1 | 7/2012 | Wittenberg | |
| 2015/0102189 A1 | 4/2015 | Klamm | |
| 2016/0074062 A1 | 3/2016 | Krupnick et al. | |
| 2016/0263310 A1 | 9/2016 | Helbig | |
| 2017/0000578 A1 | 1/2017 | Lamprooulos et al. | |
| 2019/0183607 A1 | 6/2019 | Byrne | |
| 2020/0015577 A1 | 1/2020 | Biddings, Jr. | |

OTHER PUBLICATIONS

Peel Adhesion of Pressure Sensitive Tape, Harmonized International Standard, dated Oct. 2000.

100D Premium Double-Coated Cloth Tape, Polyken, dated Jul. 28, 2015.

Tebrake, Maggie G., Selecting the Right Medical Adhesive Tape: Challenges Facing the Medical Device Designer, 3M, dated Jul./Aug. 2013.

2696P Single-Coated Woven Spec Sheet, Polyken Medical Pressure-Sensitive Tapes, dated Oct. 8, 2015.

3546P Single-Coated Woven Spec Sheet, Polyken Medical Pressure-Sensitive Tapes, dated Oct. 8, 2015.

Kato, Ryoichi et al., Radiation Dosimetry at CT Fluoroscopy: Physician's Hand Dose and Development of Needle Holders, Radiology, dated Nov. 1996.

Chenoweth, Jeffrey L, Patel, Bhargavi, Needle Holder for Use with a Biopsy Gun, dated Oct. 1991.

Stoeckelhuber, Beate M. et al., Radiation Dose to the Radiologist's Hand During Continuous CT Fluoroscopy-Guided Interventions, dated Aug. 4, 2005.

Product No. 1504XL, Hi Tack Medical Transfer Adhesive on Extended Liner, 3M Dated Jul. 2013.

Product No. 9877, Double Coated Medical Tape, 3M, Dated Nov. 2009.

Product No. 1513, Double Coated Medical Tape, 3M, Dated Jul. 2013.

Product No. 1524, Medical Transfer Adhesive, 3M, Dated Jul. 2013.

Office Action issued for U.S. Appl. No. 16/308,068, dated Oct. 27, 2020.

Notice of Allowance issued for U.S. Appl. No. 16/308,068, dated May 4, 2021.

* cited by examiner

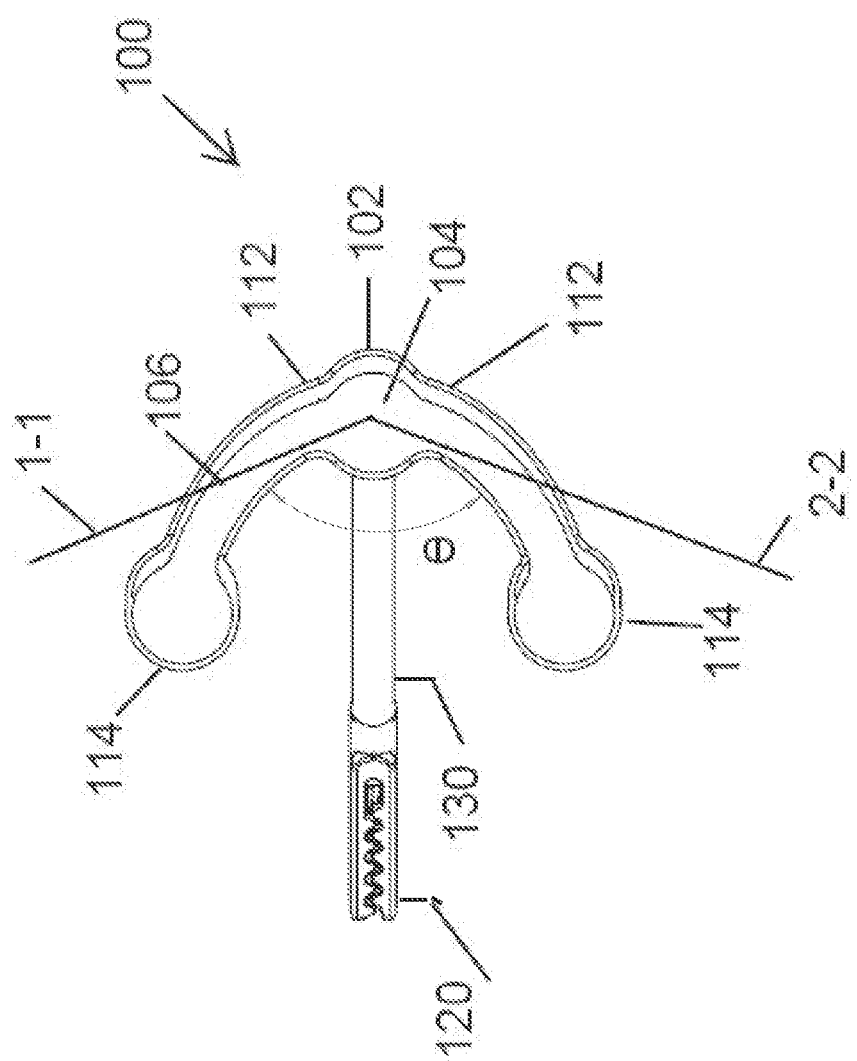

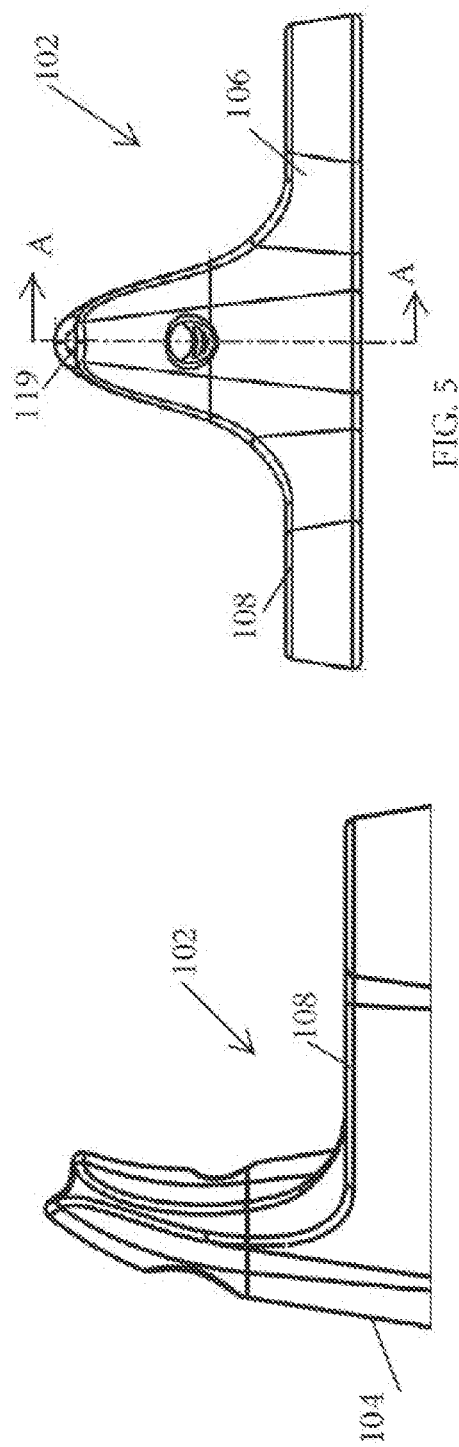
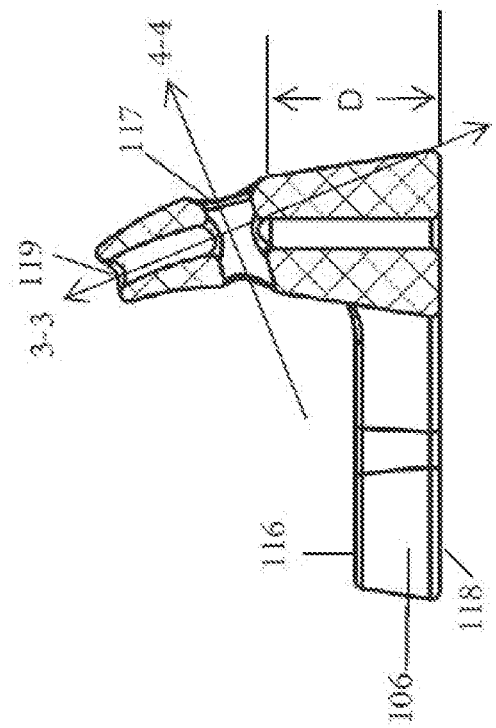

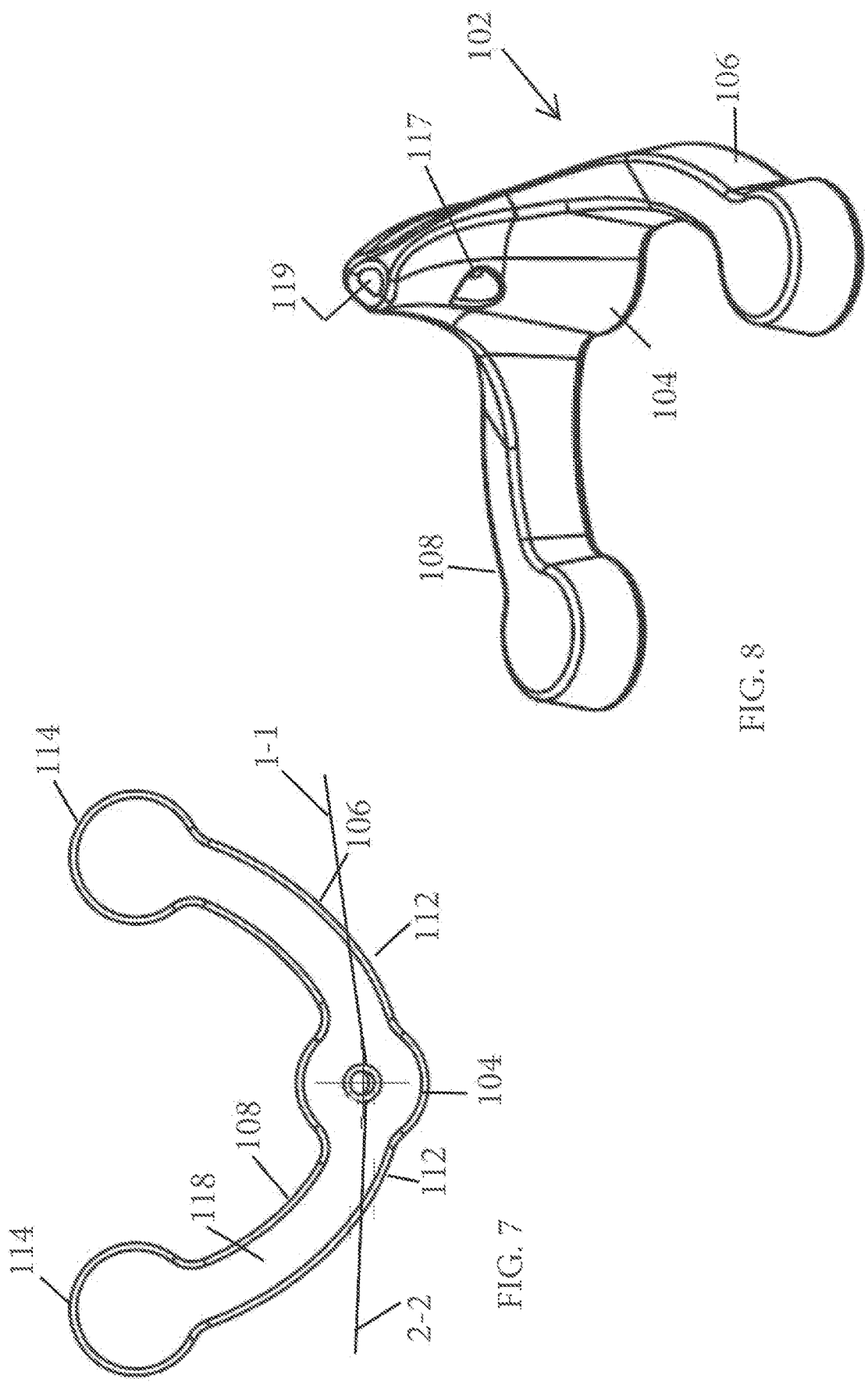

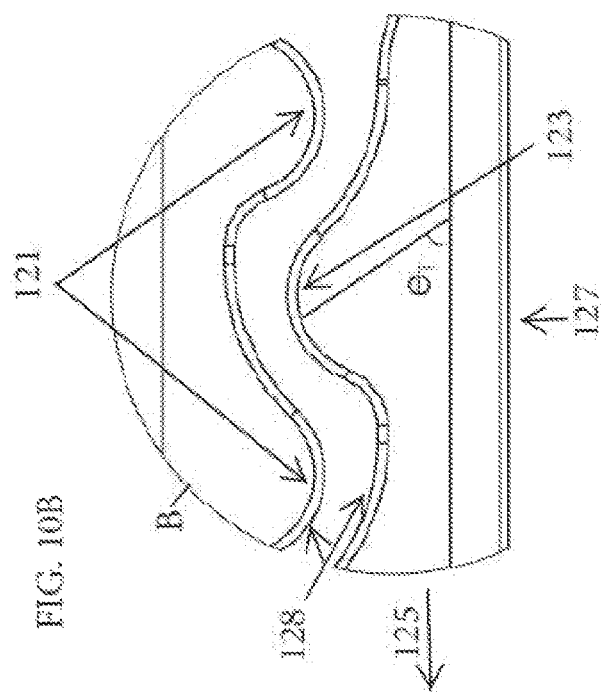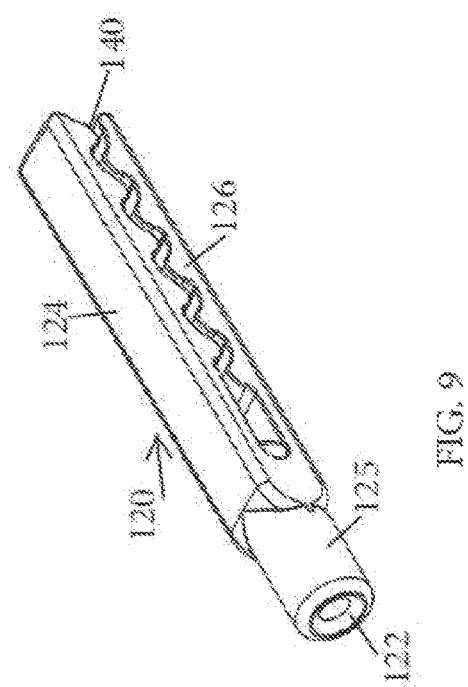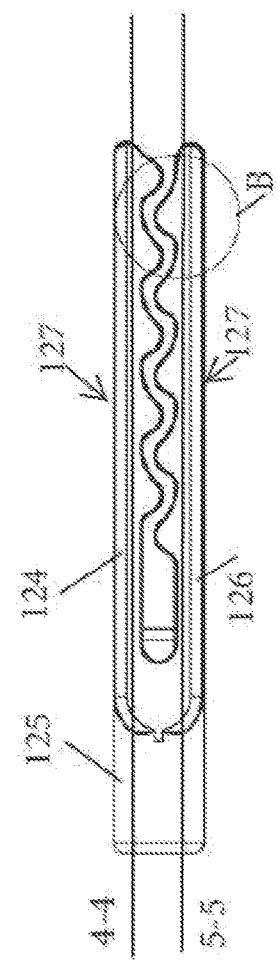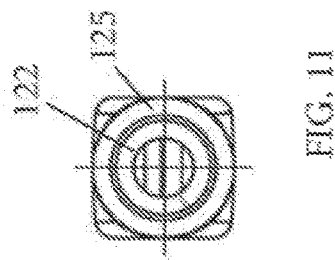

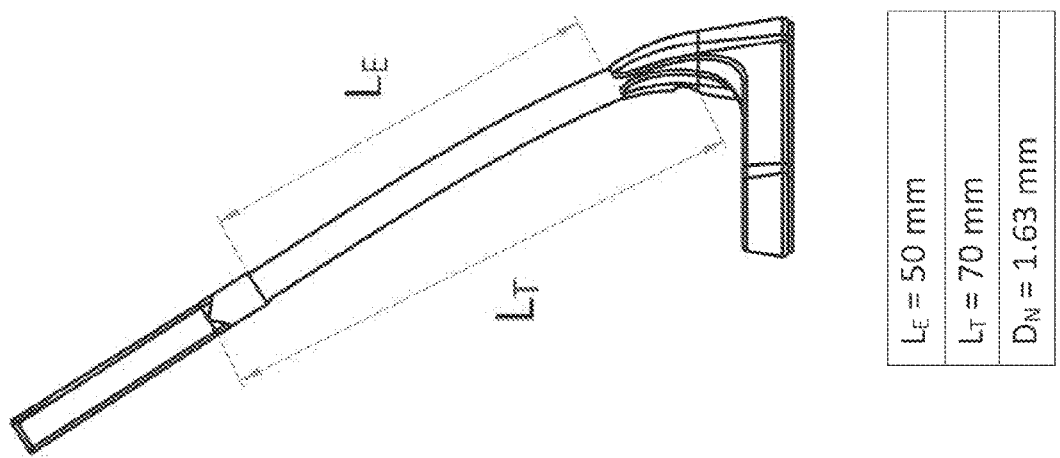
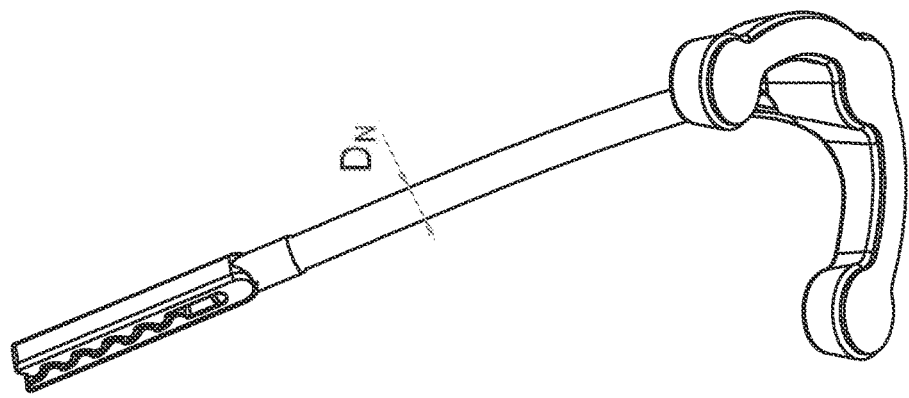
FIG. 22

DEVICES FOR SUPPORTING A MEDICAL INSTRUMENT AND METHODS OF USE

CROSS REFERENCE TO RELATED APPLICATIONS

This application is a divisional of U.S. application Ser. No. 16/308,068, filed Dec. 7, 2018, which is a United States national phase application under 35 U.S.C. § 371 of International Application No. PCT/US2018/043448, filed Jul. 24, 2018, which claims priority to U.S. Provisional Patent Application Nos. 62/649,920 and 62/650,249, both filed on Mar. 29, 2018, the contents of which are incorporated by reference herein in their entireties.

BACKGROUND

Diagnosis in medicine has been revolutionized by cross sectional imaging, such as computer tomography (CT) scanning. Use of CT scan over conventional X-ray allows physicians to look into the body with great sensitivity, which increases diagnosis of all pathophysiology from infection to cancer.

CT guided procedures utilize percutaneous needle insertion along with intermittent or continuous imaging. These procedures may require the operator to hold a needle in place while performing other tasks, including moving the patient to facilitate CT imaging and confirm placement. See Giovanna Negrão de Figueiredo & Christoph G. Trumm, *CT-Guided biopsy and drainage*, MEDICAL RADIOLOGY 1, pages 1-32 (2017). Risks associated with the procedures include radiation exposure to procedure staff and patient and procedural complications including bleeding, infection, pain, tumor seeding, pneumothorax, injury to organs, and others.

Often the highest radiation dose given current radiation protection practices is to the hands. Exposure avoidance methods including side-hand manipulation and needle stabilization devices have been implemented with mixed results. Additionally, side hand manipulation still allows high operator hand exposure. Current needle stabilization devices include towel clips and biopsy needle holders have been developed but have not gained wide usage due to several factors. Current stabilization devices are awkward as some obscure needle entry point and others have difficult release mechanisms which hinder and increase the risk of repositioning the needle during patient breathing. In addition, others limit needle excursion or create metallic artifact, which obscures biopsy target and surrounding critical structures. Several devices distance the hands spatially from the CT scanner—but must still be physically held at a distance, decreasing needle stability, rendering them less useful than radiation-reducing gloves. See Stoeckelhuber, B. M., et al., *Radiation dose to the radiologist's hand during continuous CT fluoroscopy-guided interventions*, CARDIOVASCULAR AND INTERVENTIONAL RADIOLOGY 28 (5), pages 589-94 (2005); J. L. Chenoweth & B. Patel, *Needle holder for use with a biopsy gun*, RADIOLOGY 181 (1), pages 285-86 (1991); R. Kato et al., *Radiation dosimetry at CT fluoroscopy: physician's hand dose and development of needle holders*, RADIOLOGY 201 (2), pages 576-78 (1996).

Thus, there is need in the art for a device for supporting a medical instrument and methods of use thereof that reduces complications associated with CT procedures, improves effectiveness of procedures, and reduces radiation risk to the operator.

BRIEF SUMMARY

Various implementations include methods and apparatuses for supporting a medical instrument in a position. For example, in various implementations, an apparatus includes a base having a central base portion. The base includes a first, elongated base extension protruding from the central base portion along at least a portion of a first axis and a second, elongated base extension protruding from the central base portion along at least a portion of a second axis. The first and second axes are in a base plane that extends through the central base portion, and the first and second axes intersect through the central base portion at an angle of greater than 0° and less than 180° to each other. The apparatus also includes a grasper for receiving a medical instrument and a flexible elongated neck portion having a first end and a second end. The first end of the flexible elongated neck portion is coupled with the grasper and the second end of the flexible elongated neck portion is coupled with the base. A position of the first end of the flexible elongated neck portion relative to the base is adjustable.

In some implementations, the first and second elongated base extensions are arcuate shaped as viewed in the base plane. In some implementations, the first and second elongated base extensions and the central base portion define a C-shape as viewed from the base plane.

In some implementations, the first and second elongated base extensions each have proximal and distal ends. The proximal ends are coupled to the central base portion, and the distal ends of the first and second elongated base extensions are circular shaped as viewed in the base plane.

In some implementations, each of the first and second elongated base extensions are flexible with respect to the central base portion and each other.

In some implementations, the flexible elongated neck portion is adjustable by applying pressure to an intermediate portion of the neck portion, and the intermediate portion is between the first and second ends of the neck portion.

In some implementations, the grasper defines an opening, and the first end of the flexible elongated neck portion is received within the grasper opening.

In some implementations, the flexible elongated neck portion is integrally formed with the grasper.

In some implementations, the base comprises plastic and/or metal.

In some implementations, the grasper comprises plastic and/or metal.

In some implementations, the neck portion comprises a flexible metal.

In some implementations, the neck portion has a flexural rigidity of 0.003 Pa*m$^4$ to 0.4 Pa*m$^4$.

In some implementations, the base has a first side and a second side. The first side is proximal to the second end of the flexible elongated neck portion and the second side is distal to the second end of the flexible elongated neck portion, and at least a portion of the second side lies in a plane that is parallel to the base plane. At least a portion of the second side of the base portion comprises an adhesive coating. In some implementations, the first and second elongated base extensions each have proximal and distal ends, and the proximal ends are coupled to the central base portion. The adhesive coating is disposed on at least a portion of the second side of the distal ends of the first and second elongated base extensions. In some implementations, the adhesive coating is a gel.

In some implementations, the central base portion defines an opening, and the second end of the flexible elongated neck portion is received within the base opening. In some implementations, the base has a first side and a second side. The first side is proximal to the second end of the flexible elongated neck portion and the second side is distal to the second end of the flexible elongated neck portion. At least a portion of the second side of the base lies in a plane that is parallel to the base plane. The base opening is a first base opening, and the base defines a second base opening having a central axis that is transverse to a central axis extending through the first base opening. At least a portion of a perimeter of the second base opening is spaced apart from the second side of the base by at least 5 millimeters. The second end of the flexible elongated neck portion is disposed within the first opening such that the second end does not extend past the portion of the perimeter of the second base opening.

In some implementations, the flexible elongated neck portion extends along a path such that the path is projected onto the base plane between the first and second axes, and the grasper is disposed past a plane that extends orthogonally through the base plane and tangentially to a distal end of each base extension.

In some implementations, the grasper comprises a first grasper portion, a second grasper portion, and a central grasper portion. The first and second grasper portions extend from the central grasper portion along first and second grasper axes, respectively, and the grasper axes lie within a grasper plane. The medical instrument is receivable between the first and second grasper portions.

In some implementations, the grasper includes a first grasper portion and a second grasper portion. The first and second grasper portions each have an inner surface and an outer surface, and the inner surface and the outer surface of each of the first and second grasper portions are spaced apart and opposite each other. The inner surfaces of the first and second grasper portions face each other. A central grasper portion extends between the first and second grasper portions. The first grasper portion extends along a first grasper axis and the second grasper portion extends along a second grasper axis. The grasper axes lie within a grasper plane that extends through the central grasper portion. The medical instrument is receivable between the inner surfaces of the first and second grasper portions.

In some implementations, the inner surface of the first grasper portion comprises a first set of teeth and the inner surface of the second grasper portion comprises a second set of teeth. In some implementations, a contour of the first set of teeth correspond with a contour of the second set of teeth, and troughs of the first set of teeth are disposed between peaks of the second set of teeth, and vice versa. In some implementations, the first and second sets of teeth have a contour that is pitched toward the central grasper portion at an angle less than 90°, such that advancement of the medical instrument between the inner surfaces of the first and second grasper portions in a direction toward the central grasper portion produces less resistance than retraction of the medical instrument between the inner surfaces of the first and second grasper portions in a direction away from the central grasper portion.

In some implementations, the inner surfaces of the first and second grasper portions comprise a frictional coating for gripping.

In some implementations, the grasper includes a first grasper portion and a second grasper portion. The first and second grasper portions each have an inner surface and an outer surface, and the inner surface and the outer surface of each of the first and second grasper portions are spaced apart and opposite each other. The inner surfaces of the first and second grasper portions face each other. A central grasper portion extends between the first and second grasper portions. The first grasper portion extends along a first grasper axis and the second grasper portion extends along a second grasper axis. The first and second grasper axes lie within a grasper plane that extends through the central grasper portion. Distal ends of the first and second grasper portions are spaced apart from the central grasper portion along the first and second grasper axes, respectively. The distal ends of the first and second grasper portions are biased toward each other into a first position and urgable away from each other into a second position. The medical instrument is receivable between the inner surfaces of the first and second grasper portions.

In some implementations, each of the first and second grasper portions includes an engagement portion that is spaced apart from the distal end of each of the first and second grasper portions along the respective grasper axes. The central grasper portion is coupled to each of the first and second grasper portions between the distal end and engagement portion of each of the first and second grasper portions. The engagement portions are urgable toward each other to urge the distal ends of the first and second grasper portions away from each other.

In some implementations, the inner surfaces of the first and second grasper portions comprise a frictional coating for gripping.

Other various implementations include a device for supporting a medical instrument in a position. The device includes a base, a flexible elongated neck portion, and a grasper for receiving the medical instrument. The grasper includes a first grasper portion and a second grasper portion. The first and second grasper portions each have an inner surface and an outer surface, and the inner surface and the outer surface of each of the first and second grasper portions are spaced apart and opposite each other. The inner surfaces of the first and second grasper portions face each other. A central grasper portion extends between the first and second grasper portions. The first grasper portion extends along a first grasper axis and the second grasper portion extends along a second grasper axis. The first and second grasper axes lie within a grasper plane that extends through the central grasper portion. Distal ends of the first and second grasper portions are spaced apart from the central grasper portion along the first and second grasper axes, respectively. The distal ends of the first and second grasper portions are biased toward each other into a first position and urgable away from each other into a second position. The medical instrument is receivable between the inner surfaces of the first and second grasper portions.

Other various implementations include a device for supporting a medical instrument in a position. The device includes a base, a flexible elongated neck portion, and a grasper for receiving the medical instrument. The grasper includes a first grasper portion and a second grasper portion. The first and second grasper portions each have an inner surface and an outer surface, and the inner surface and the outer surface of each of the first and second grasper portions are spaced apart and opposite each other. The inner surfaces of the first and second grasper portions face each other. The device also includes a central grasper portion. The first and second grasper portions extend from the central grasper portion along first and second grasper axes, respectively. The grasper axes lie within a grasper plane that extends through the central grasper portion. The medical instrument is receivable between the inner surfaces of the first and second grasper portions. The inner surface of the first grasper portion includes a first set of teeth and the inner surface of the second grasper portion comprises a second set of teeth. The flexible elongated neck portion extends between the base and the grasper.

In some implementations, the first and second sets of teeth have a contour that is pitched toward the central grasper portion at an angle less than 90°, such that advancement of the medical instrument between the inner surfaces of the first and second grasper portions in a direction toward the central grasper portion produces less resistance than retraction of the medical instrument between the inner surfaces of the first and second grasper portions in a direction away from the central grasper portion.

Other various implementations include a device for supporting a medical instrument. The device includes a base having a first side and a second side. The first and second sides are opposite and spaced apart from each other. The device also includes a grasper for receiving a medical instrument and a flexible elongated neck portion. The flexible elongated neck portion has a first end and a second end. The first end is coupled to the grasper and the second end is coupled to the first side of the base holder. The second end is spaced apart from the second side at least 5 mm.

Other various implementations include a method of positioning a medical needle. The method includes the steps of (1) positioning the medical needle relative to a patient's skin; (2) coupling a device for supporting the medical instrument to the patient's skin, the device including a base for coupling to the patient's skin, a flexible, elongated neck portion, and a grasper, the flexible, elongated neck portion extending between the base and the grasper; and (3) coupling the grasper to the medical needle. The step of coupling the device to the patient's skin or coupling the grasper to the medical needle occurs after positioning the medical needle relative to the patient's skin.

BRIEF DESCRIPTION OF THE DRAWINGS

Various implementations are explained in even greater detail in the following example drawings. The drawings are merely examples to illustrate the structure of various devices and certain features that may be used singularly or in combination with other features. The claims should not be limited to the implementations shown. Features shown are not necessarily drawn to scale.

FIG. 3 shows a bottom view of the device in FIG. 1.

FIG. 4 shows a left side view of a base of the device in FIG. 1.

FIG. 5 shows a rear view of the base in FIG. 4.

FIG. 6 shows a cross sectional side view through the A-A line shown in FIG. 5.

FIG. 7 shows a bottom view of the base in FIG. 4.

FIG. 8 shows a perspective front view of the base in FIG. 4.

FIG. 9 shows a top perspective view of a grasper of the device shown in FIG. 1.

FIG. 10A shows a top view of the grasper in FIG. 9, and FIG. 10B shows a close up of portion B encircled on the grasper in FIG. 9.

FIG. 11 shows a rear view of the grasper in FIG. 9.

FIG. 12 shows a right side view of the grasper in FIG. 9. The left side view of the grasper is the same as the right side view.

FIGS. 22-24 show example dimensions of the device in FIGS. 1-18.

DETAILED DESCRIPTION

Figure 1:
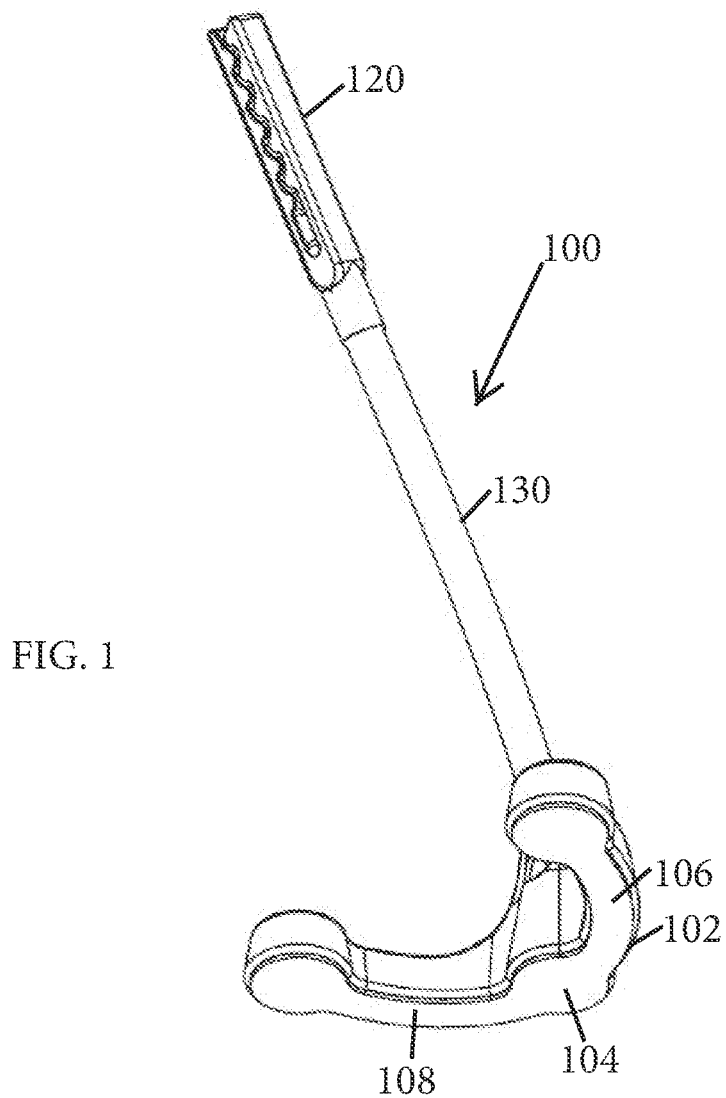
FIG. 1 shows a bottom perspective view of a device according to one implementation.
Figure 2:
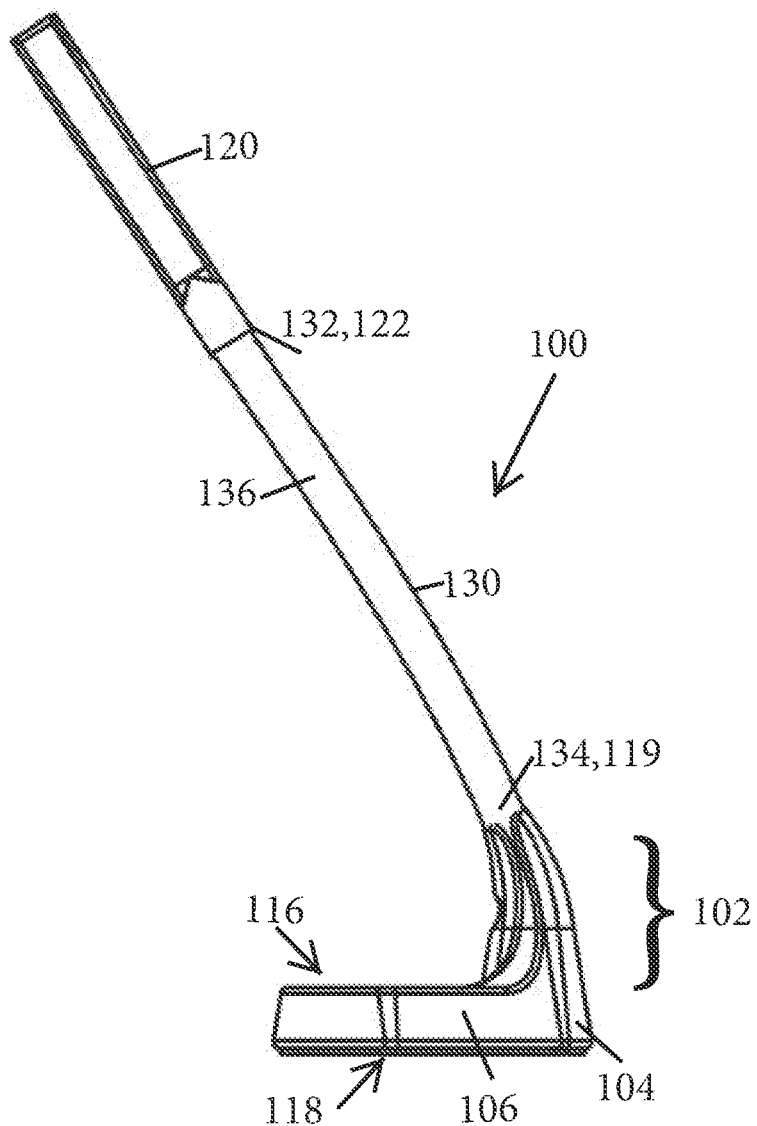
FIG. 2 shows a right side view of the device in FIG. 1.
Figure 13:
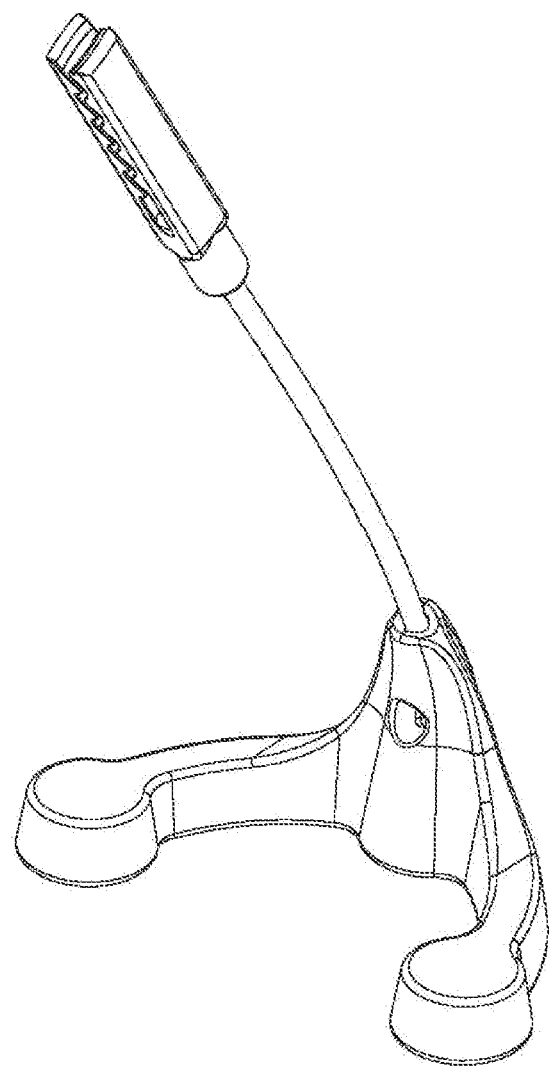
FIG. 13 shows a front perspective view of the device in FIG. 1 with a coating.

Various implementations include a device for holding and supporting a medical instrument 10 in a position. For example, the medical instrument 10 may include a percutaneous procedure apparatus, such as a needle (e.g., biopsy needle, anesthesia needle) or needle holder. In some implementations, the device holds and supports the percutaneous procedure apparatus and liberates the procedure operator's hands from direct beam exposure, which lowers the risk of complications and radiation exposure to patients and procedure operators. The device also increases the effectiveness of the procedure by holding and supporting the apparatus in the intended position.

Examples of a percutaneous procedure apparatus include a biopsy needle, such as a 21 g FNA to a 11 g bone biopsy trocar.

Various implementations of the device have sufficient flexibility and stability to hold and support the percutaneous procedure apparatus in the intended position, regardless of patient position, during a scanning procedure (e.g., CT scan). For example, at least a portion of the device is made of a bendable material, which allows the portion of the device to be moved to the appropriate angle or configuration and hold that configuration during the procedure, and at least a portion of the device is adherable to the patient's skin to keep the device in place relative to the patient's skin. The device allows the operator to remove his or her hands from near the field being scanned, which reduces the operator's exposure to radiation.

For example, in the implementation shown in FIGS. 1-18, the device 100 includes a base 102, a grasper 120 for receiving the medical instrument 10, and a flexible elongated neck portion 130. The base 102 includes a central base portion 104, a first, elongated base extension 106 protruding from the central base portion 104 along at least a portion of a first axis 1-1, and a second, elongated base extension 108 protruding from the central base portion 104 along at least a portion of a second axis 2-2. The first and second axes 1-1, 2-2 are in a base plane that extends through the central base portion 104. And, the first and second axes 1-1, 2-2 extend through the central base portion 104 and intersect each other at an angle θ of greater than 0° and less than 180°. The axes 1-1 and 2-2 may intersect within a perimeter of the central base portion 104 or outside of it.

In the implementation shown, the first 106 and second elongated base extensions 108 are arcuate shaped as viewed in the base plane. For example, as shown, the first 106 and second elongated base extensions 108 and the central base portion 104 define a C-shape as viewed from the base plane. Thus, a full length of each extension 106, 108 does not extend along the respective axes 1-1, 2-2. However, in other implementations, the full length (or more of the length) of each extension 106, 108 may extend along the respective axes 1-1, 2-2. In addition, in other implementations, the shape of the base extensions 106, 108 may be selected to provide a sufficient amount of surface area for coupling to the patient's skin and for supporting the stability of the neck portion 130 and grasper 120. For example, the base extensions 106, 108 may form an annular ring or a semi-annular ring or may have an undulating perimeter shape (e.g., S-shaped).

The first 106 and second elongated base extensions 108 each have proximal 112 and distal ends 114. The proximal ends 112 are coupled to the central base portion 104, and the distal ends 114 of the first 106 and second elongated base extensions 108 are circular shaped as viewed in the base plane. This circular shape provides additional surface area for applying pressure to adhere the distal ends 114 to the patient's skin and for holding the base in place while adjusting the neck portion 130. However, in other implementations, the distal ends 114 may have other suitable shapes that are wider than the elongated base portions to provide additional surface area for applying pressure to adhere the distal ends 114 to the patient's skin and for holding the base in place while adjusting the neck portion 130. Other suitable shapes may include semi-annular, trapezoidal, rectangular, or other suitable closed two-dimensional shape as viewed from the base plane. And, in some implementations, the distal ends 114 are not wider than the other portions of the elongated base portions if the width of the distal end is sufficient to adhere to the skin and provide a sufficient surface against which the user can stabilize the base while adjusting the neck portion 130.

Figure 23:
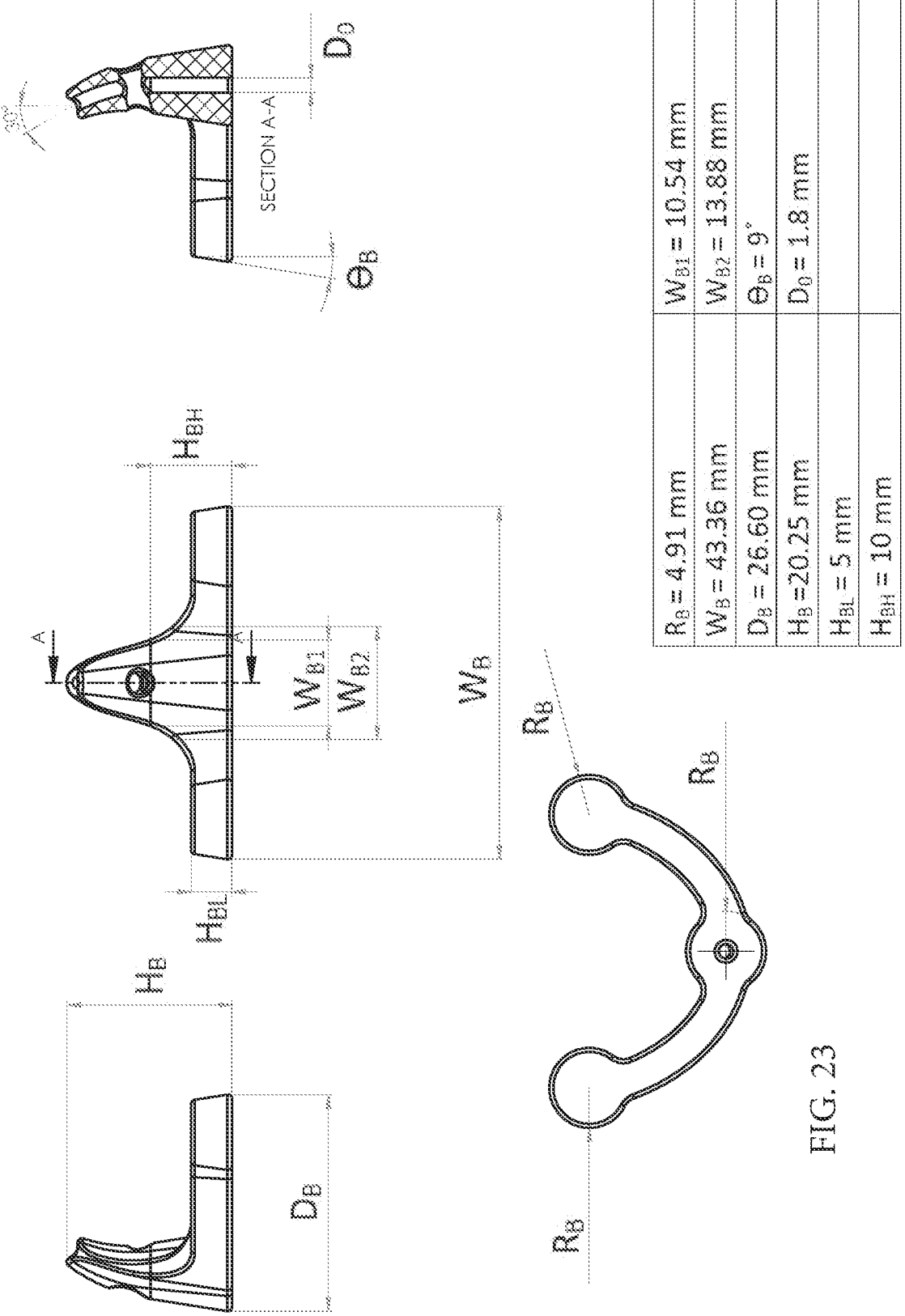

In addition, the base 102 includes a first side 116 and a second side 118. The second side 118 is opposite and spaced apart from the first side 116, and the second side lies within a plane that is parallel to the base plane. In some implementations, a side surface of each base extension 106, 108 extending between the first side 116 and the second side 118 adjacent the distal ends 114 tapers outwardly from the first side 116 to the second side 118. For example, a plane tangential to the distal ends 114 may intersect the base plane at an angle of 81°, as shown in FIG. 23. In addition, a length LB between distal edges of distal ends 114 of the base extensions 106, 108 and a distal edge of the central base portion 104 is about ¼ to ¾ (e.g., ½) of the exposed length LE of the neck portion 130, wherein the exposed length is the length of the neck portion 130 that is between the base 102 and the grasper 120.

In some implementations, an adhesive coating is disposed on at least a portion of the second side 118. The portions to be coated with the adhesive coating may be spaced apart from each other to increase the stability of the device. For example, in certain implementations, the adhesive coating is disposed on at least a portion of the second side of the distal ends 114 of the first 106 and second elongated base extensions 108 and the central base portion 104. In some implementations, the adhesive coating may be disposed on the entire second side 118.

In some implementations, the adhesive coating for adhering to the patient's skin may be a medical grade pressure sensitive adhesive with a high peel adhesion strength and that is compatible with sterilization methods (e.g., rubbing alcohol on the patient's skin prior to applying the adhesive coating), breathable, has relatively high initial tack, and results in low skin trauma. The adhesive is not repositionable in some implementations, but the adhesive is repositionable in other implementations.

In some implementations, the adhesive coating is a gel (e.g., silicone gel), an acrylate adhesive (e.g., 3M 9907HTW hi tack non-woven medical tape from 3M, 3M 1513 double coated medical tape from 3M, 3M 1524 medical transfer adhesive from 3M), a synthetic rubber adhesive, or a rubber adhesive (e.g., 3M 9877 double coated medical tape from 3M, 3M 1504XL hi tack medical transfer adhesive on extended liner tape from 3M, Polyken 100D double-coated cloth tape from Berry Plastics, Polyken 2696P single-coated medical woven fabric tape from Berry Plastics, and Polyken 3546P stretchable woven single-sided tape from Berry Plastics).

As noted above, in certain implementations, the adhesive coating includes a double-sided tape that includes backer paper on each side that is removable before adhering to the second side 118 of the base 102 or the patient's skin. However, in other implementations, the adhesive coating may include one or more adhesive materials coupled together.

Furthermore, in some implementations, the adhesive coating has a peel adhesion to stainless steel of at least 40 oz/in width at 180° peel angle, as measured by ASTM D3330/D3330M-04 and PSTC-101 as published in May 2007. Furthermore, in some implementations, the adhesive coating has a peel adhesion to stainless steel of less than 210 oz/in width at 90° peel angle and/or less than 130 oz/in width at 180° peel angle. These ranges are examples, and other suitable ranges may be suitable for use with this device.

The central base portion 104 defines a first opening 119 that extends along an axis 3-3 that is transverse to the base plane. For example, in the implementation shown, the axis 3-3 is disposed at an angle of 60° with the baseplane. In addition, the central base portion 104 defines a second opening 117 that extends along an axis 4-4 that is transverse to the axis 3-3. At least a portion of a perimeter P of the second base opening 117 is spaced apart from the second side 118 of the base 102 by a distance d of at least 5 millimeters (e.g., 10 mm as shown in FIG. 23). This opening 117 allows for the operator to view the second end 134 of the flexible neck portion 130 as it is engaged into the opening 119 and ensure that the second end 134 does not extend past the opening 117. For a neck portion 130 made of aluminum, having the second end 134 of the neck portion 130 closer than 5 mm to the skin can cause X-ray scatter toward the lesion. This distance d may be increased or decreased depending on the material of at least the distal end of the flexible elongated neck portion, for example. For example, in some implementations, a portion of the perimeter of the second base opening 117 may intersect a plane that includes the second side 118 of the base 102 (i.e., d is 0 mm). In addition, an external surface of the central base portion 104 may taper outwardly from an upper portion thereof that defines the first opening 119 toward a lower portion thereof from which the base extensions 106, 108 extend.

In some implementations, the base 102 includes a plastic and/or metal material. For example, in some implementations, the base 102 is aluminum cast, and then the base 102 is coated in a plastic material. The aluminum cast and plastic material are selected such that the first 106 and second elongated base extensions 108 are firm but flexible with applied force with respect to the central base portion 104 and each other, according to some implementations. In other implementations, the base 102 is an injection molded plastic component, and in certain implementations, the plastic is selected such that the first 106 and second elongated base extensions 108 are firm but flexible with applied force with respect to the central base portion 104 and each other. And, in some implementations, the base extensions 106, 108 are not flexible relative to each other and the central base portion 104.

The flexible elongated neck portion 130 has a first end 132 and a second end 134 and an intermediate portion 136 disposed between the first end 132 and the second end 134. The first end 132 is coupled with the grasper 120, and the second end 134 is coupled with the base 102.

The neck portion comprises a flexible metal, such as aluminum. For example, the neck portion has a flexural rigidity of 0.003 Pa*m$^4$ to 0.4 Pa*m$^4$ (e.g., 0.0037 Pa*m$^4$ to 0.28 Pa*m$^4$). The flexural rigidity refers to the force couple required to bend a non-rigid structure one unit of curvature. In other words, it is the resistance offered by a structure (such as the neck portion 130) while undergoing bending. The flexural rigidity is measured in SI units of Pa·m$^4$ and is the product of the elastic modulus (E) of the material and the second moment of inertia (I). A position of the first end 132 of the flexible elongated neck portion 130 relative to the second end 134 is adjustable by applying pressure to the intermediate portion 136 of the neck portion 130. By selecting one or more materials and/or dimensions of the neck portion to increase the flexural rigidity, the neck portion deforms less under an equal load. For example, to reduce deformation of the neck portion, a material with a higher E and/or dimensions that yield a higher I may be selected. Conversely, to increase the deformation of the neck portion, a material with a lower E and/or dimensions that yield a lower I may be selected. In certain implementations, for example, 1100 aluminum wire may be selected for the neck portion, which has an elastic modulus E of 70-80 GPa at 25° C. The diameter of the wire may be between 0.040" to 0.114", which yields a flexural rigidity of between 0.0037 Pa*m$^4$ and 0.28 Pa*m$^4$.

In the implementation shown in FIGS. 9-12, the grasper 120 comprises a first grasper portion 124, a second grasper portion 126, and a central grasper portion 125. The central grasper portion 125 extends between the first 124 and second grasper portions 126 and defines an opening 122 for receiving the first end 132 of the neck portion 130. The first grasper portion 124 extends along a first grasper axis 5-5 and the second grasper portion 126 extends along a second grasper axis 6-6. The grasper axes 5-5, 6-6 lie within a grasper plane that extends through the central grasper portion 125, and the axes 5-5, 6-6 are parallel to each other. The medical instrument is receivable between the first 124 and second grasper portions 126.

The first 124 and second grasper portions 126 each have an inner surface 128 and an outer surface 127. The inner surface 128 and the outer surface 127 of each of the first 124 and second grasper portions 126 are spaced apart and opposite each other. The inner surfaces 128 of the first 124 and second grasper portions 126 face each other.

In the implementation shown in FIGS. 9-12, the inner surface 128 of the first grasper portion 124 comprises a first set of teeth 121, and the inner surface 128 of the second grasper portion 126 comprises a second set of teeth 123. For example, as shown, each surface 128 has five teeth. A contour of the first set of teeth 121 correspond with a contour of the second set of teeth 123. For example, peaks of the set of teeth 121 are disposed within troughs defined by peaks of the set of teeth 123, and vice versa, and the inner surfaces 128 are spaced apart. The distance between portions of the inner surfaces 128 may be varied to accommodate medical instruments of different diameters. In addition, the first 121 and second sets of teeth 123 have a contour that is pitched toward the central grasper portion 125 at an angle $\theta_T$ less than 90°, such that advancement of the medical instrument 10 between the inner surfaces 128 of the first 124 and second grasper portions 126 in a direction toward the central grasper portion 125 produces less resistance than retraction of the medical instrument 10 between the inner surfaces 128 of the first 124 and second grasper portions 126 in a direction away from the central grasper portion 125. Furthermore, the inner surfaces 128 of the first 124 and second grasper portions 126 comprise a frictional coating for gripping the medical instrument 10. In use, the distal end 140 of the grasper 120 defines an opening between the inner surfaces 128, and the grasper 120 is moved toward the needle 10 by pushing on the neck portion 130 to engage the needle 10 between the sets of teeth 121, 123.

Figure 21:
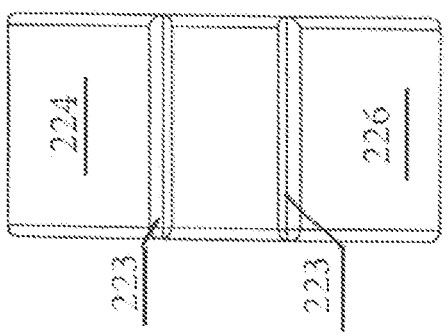
FIG. 21 shows a front view of the grasper in FIG. 19.
Figure 20:
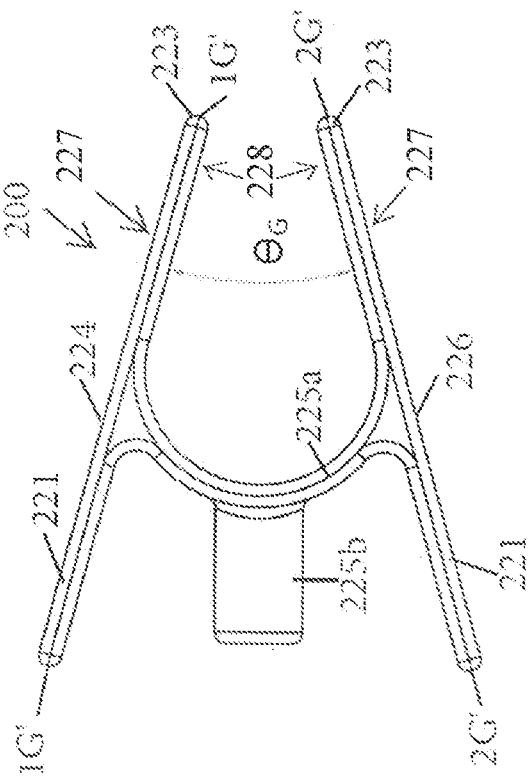
FIG. 20 shows a top view of the grasper in FIG. 19.
Figure 19:
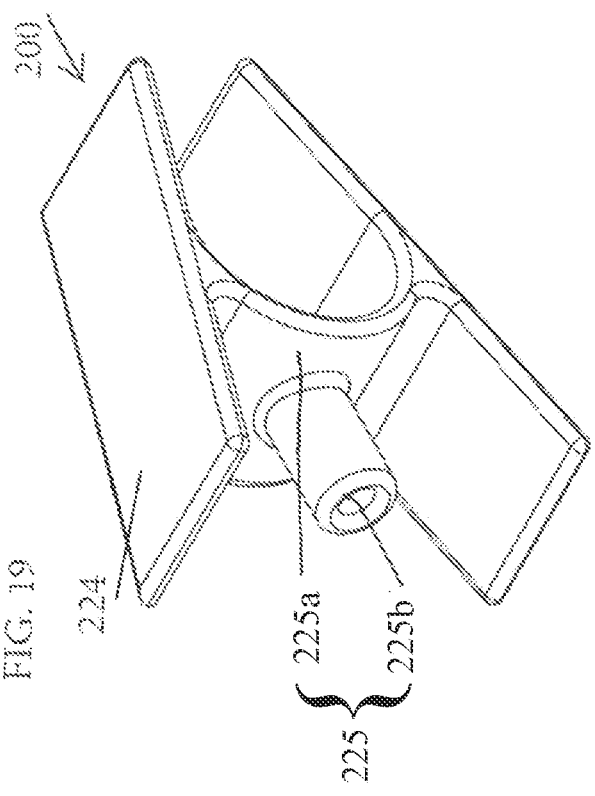
FIG. 19 shows a perspective top view of a grasper according to another implementation.

An alternative implementation of the grasper is shown in FIGS. 19-21. In this implementation, grasper 200 includes a first grasper portion 224, a second grasper portion 226, and a central grasper portion 225. The first 224 and second grasper portions 226 each have an inner surface 228 and an outer surface 227. The inner surface 228 and the outer surface 227 of each of the first 224 and second grasper portions 226 are spaced apart and opposite each other. The inner surfaces 228 of the first 224 and second grasper portions 226 face each other. The central grasper portion 225 extends between the first 224 and second grasper portions 226. The first grasper portion 224 has a central axis 1G'-1G', and the second grasper portion 226 has a central axis 2G'-2G'. The axes 1G'-1G' and 2G'-2G' lie within a grasper plane that extends through the central grasper portion 225. Distal ends 223 of the first 224 and second grasper portions 226 are spaced apart from the central grasper portion 225, and the distal ends 223 of the first 224 and second grasper portions 226 are biased toward each other in a first position about the central grasper portion 225, which is shown in FIGS. 19-21. The axes 1G'-1G' and 2G'-2G' intersect an angle $\theta_G$ that is greater than 0° and less than 90° (e.g., 30°) at a point that is forward of the central grasper portion 225 and the distal ends 223 in the biased position. The distal ends 223 are urgable away from each other into a second position (not shown) by urging engagement portions 221 of each of the first 224 and second grasper portions 226 toward each other (e.g., by pinching the engagement portions 221 toward each other). The engagement portions 221 are spaced apart from the distal ends 223 along the respective axes, and the central grasper portion 225 is coupled to each grasper portion 224, 226 between the engagement portion 221 and distal end 223. In the implementation shown, the central grasper portion 225 comprises a flexible, arcuate shaped portion 225a and a cylindrically shaped boss 225b that extends from the arcuate shaped portion 225a and is disposed between the engagement portions 221. The medical instrument 10 is receivable between the inner surfaces 228 of the first 224 and second grasper portions 226 between the distal ends 223 and the central grasper portion 225. In addition, the inner surfaces 228 of the first 224 and second grasper portions 226 comprise a frictional coating for gripping the medical instrument 10.

Figure 24:
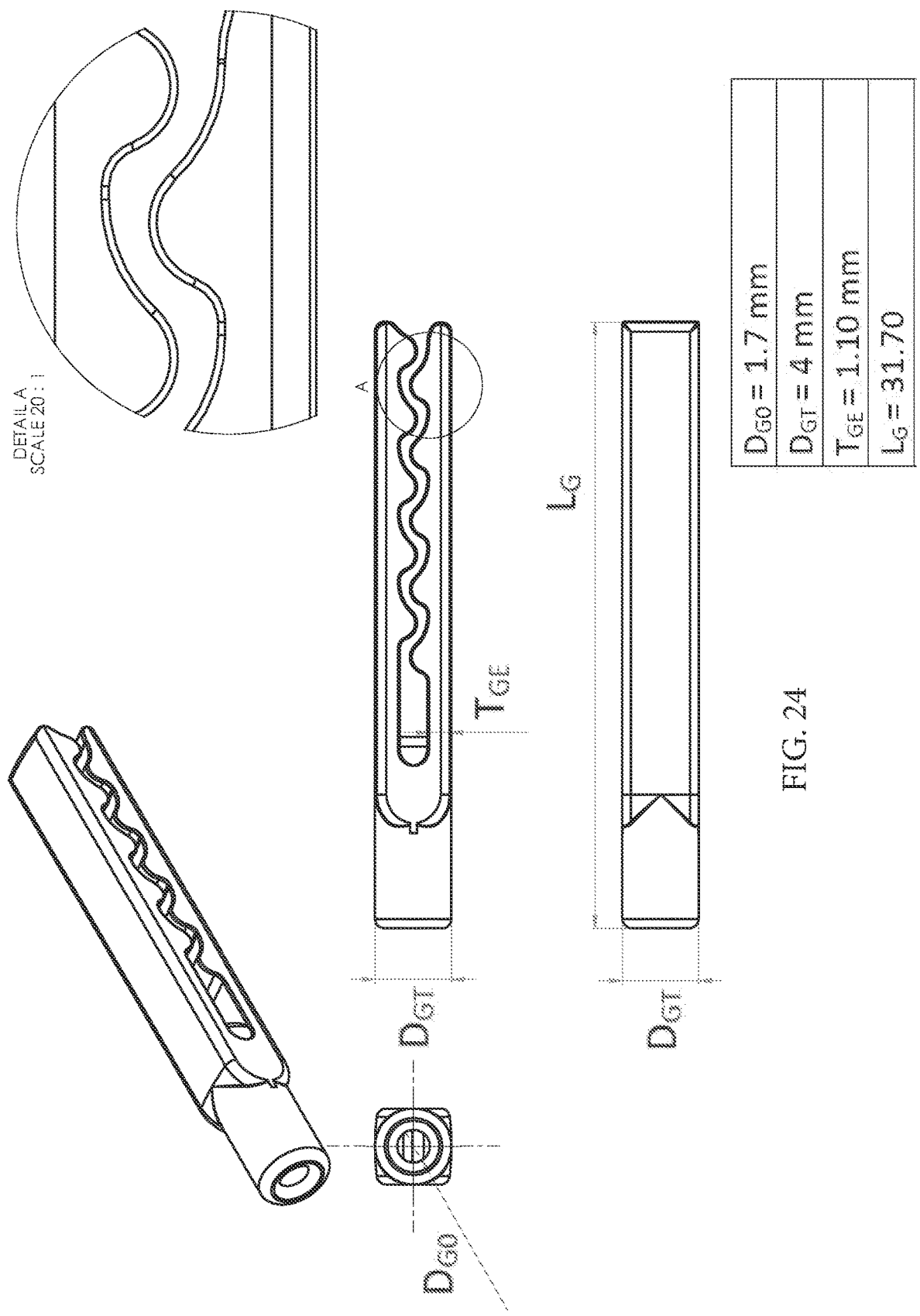
Figure 25:
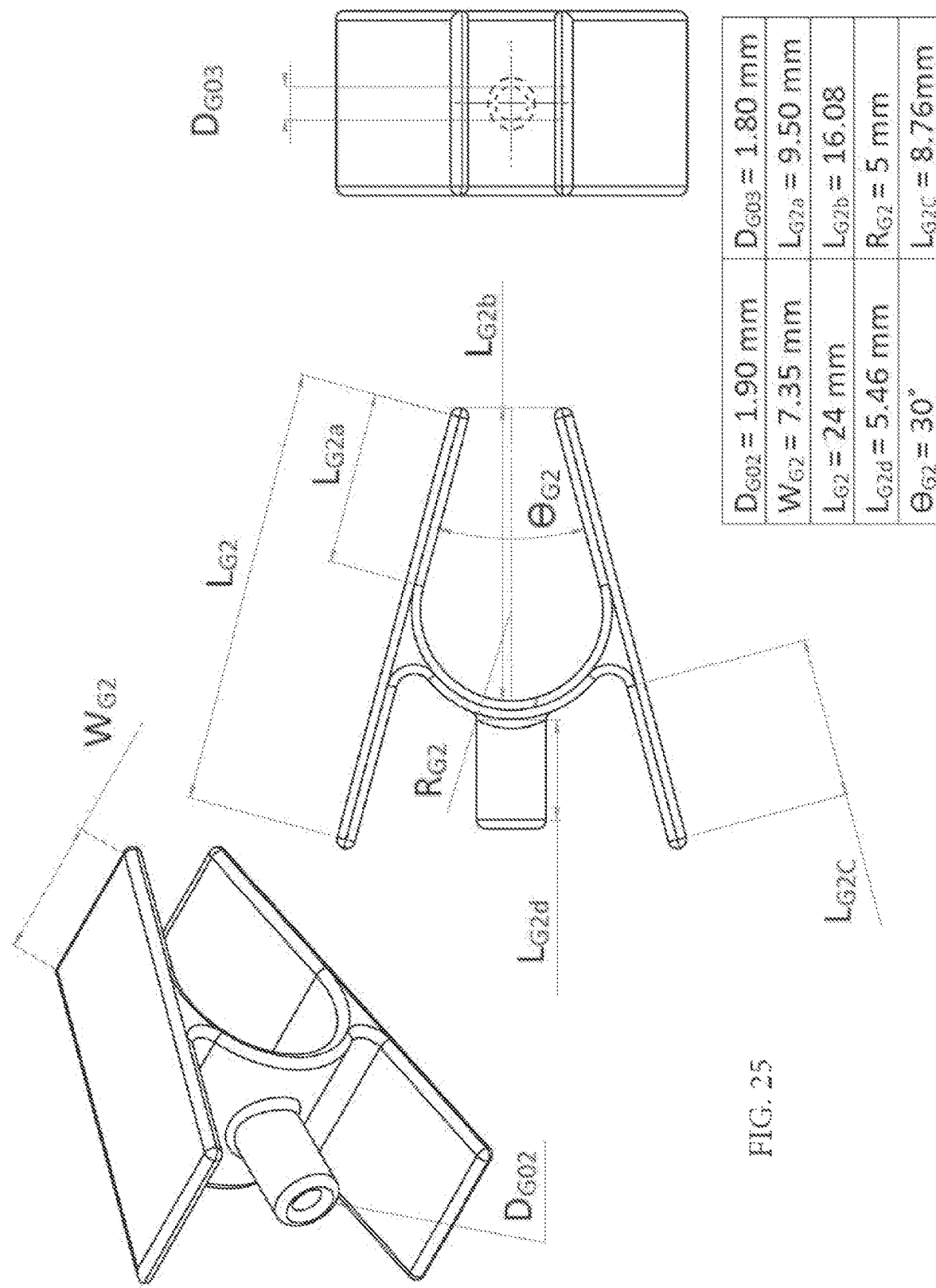
FIG. 25 shows example dimensions of the grasper in FIGS. 19-21.

FIGS. 22-24 illustrate example dimensions of the device 100 shown in FIGS. 1-18, and FIG. 25 illustrates example dimensions of the grasper 200 shown in FIGS. 19-21. The dimensions shown are examples and should not limit the scope of the claims.

To assemble the device 100, the second end 134 of the flexible elongated neck portion 130 is disposed (e.g., press-fit, threaded) within the first base opening 119. The first side 116 of the base 102 is proximal to the second end 134 of the flexible elongated neck portion 130, and the second side 118 is distal to the second end 134 of the flexible elongated neck portion 130. The second end 134 of the flexible elongated neck portion 130 is disposed within the first base opening 119 such that the second end 134 does not extend past the portion of the perimeter P of the second base opening 117, as noted above.

The flexible elongated neck portion 130 extends along a path such that the path is projected onto the base plane between the first 1-1 and second axes 2-2, and the grasper 120 is disposed past a plane that extends orthogonally through the base plane and tangentially to the distal end 114 of each base extension 106, 108.

The first end 132 of the flexible elongated neck portion 130 is disposed (e.g., press-fit, threaded) within the grasper opening 122. However, in some implementations, the flexible elongated neck portion 130 is integrally formed with the grasper 120. And, in some other implementations, the second end 134 of the neck portion 130 may define a channel that receives a protrusion extending from the base 102 to engage the base 102 and the neck portion 130. Similarly, in other implementations, the first end 132 of the neck portion 130 may define a channel that receives a protrusion extending from the grasper 122.

Figure 14:
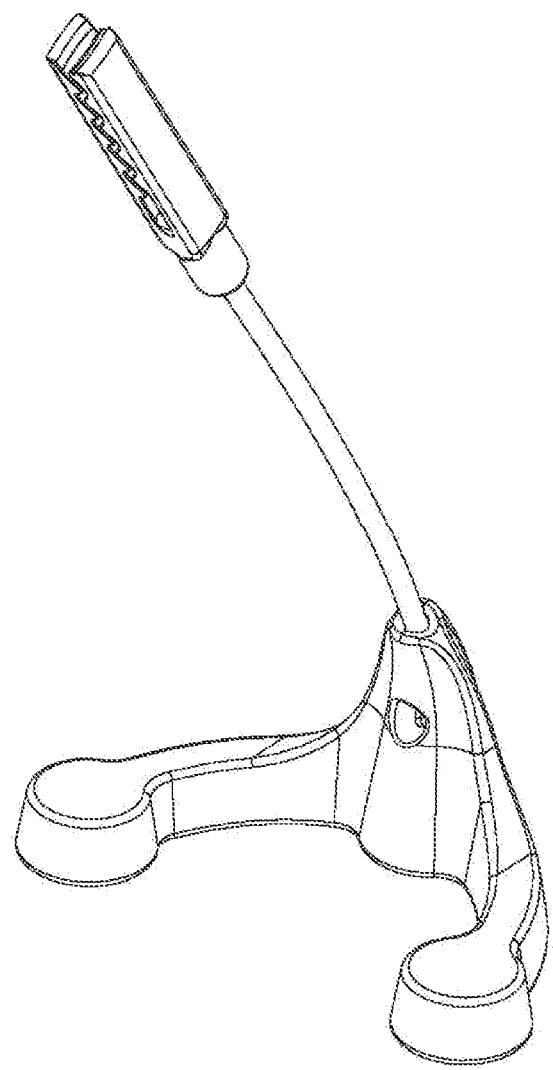
FIG. 14 shows a front perspective view of the device in FIG. 1 without the coating.
Figure 15:
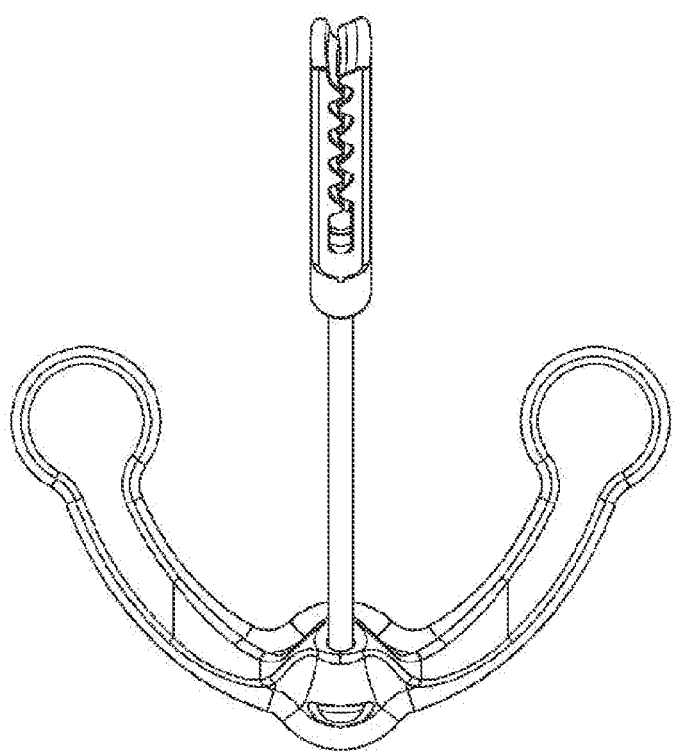
FIG. 15 shows a top view of the device in FIG. 13.
Figure 16:
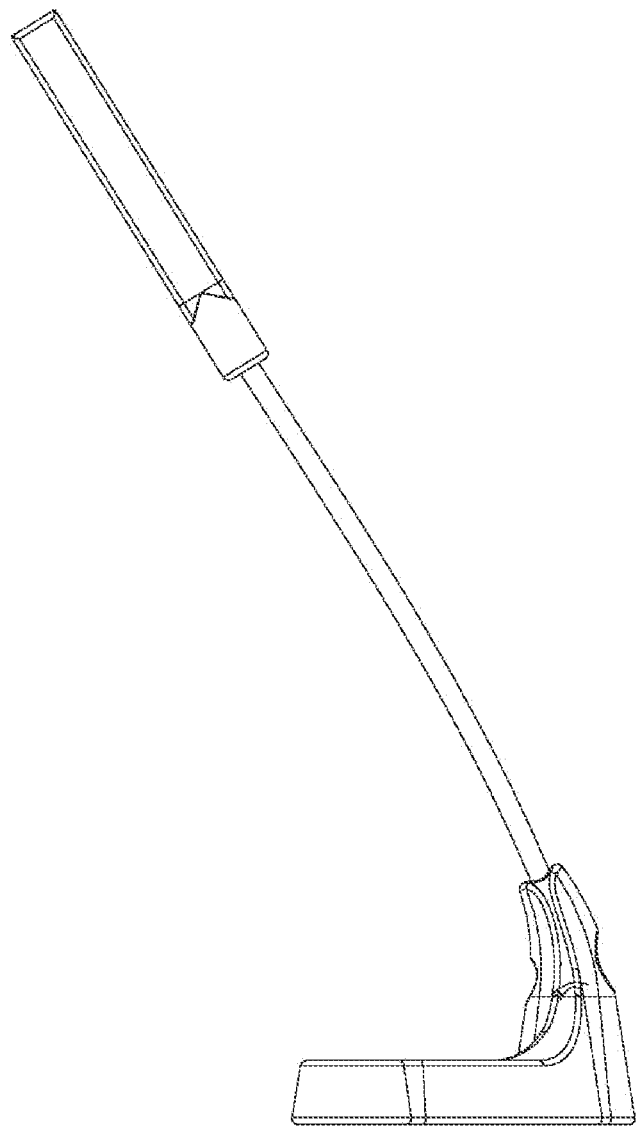
FIG. 16 shows a right side view of the device in FIG. 13. The left side view of the device is the same as the right side view.
Figure 17:
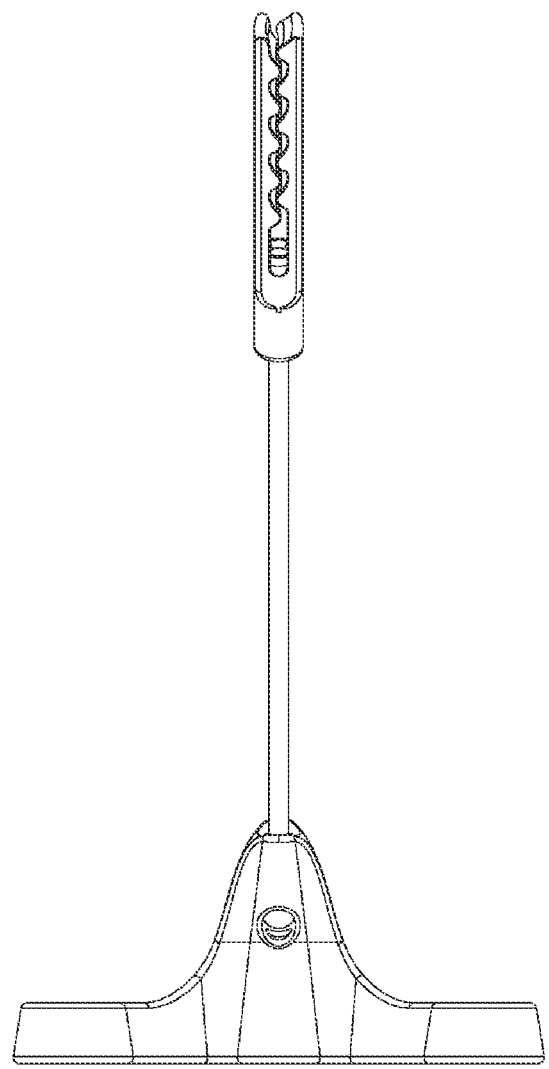
FIG. 17 shows a front view of the device in FIG. 13.
Figure 18:
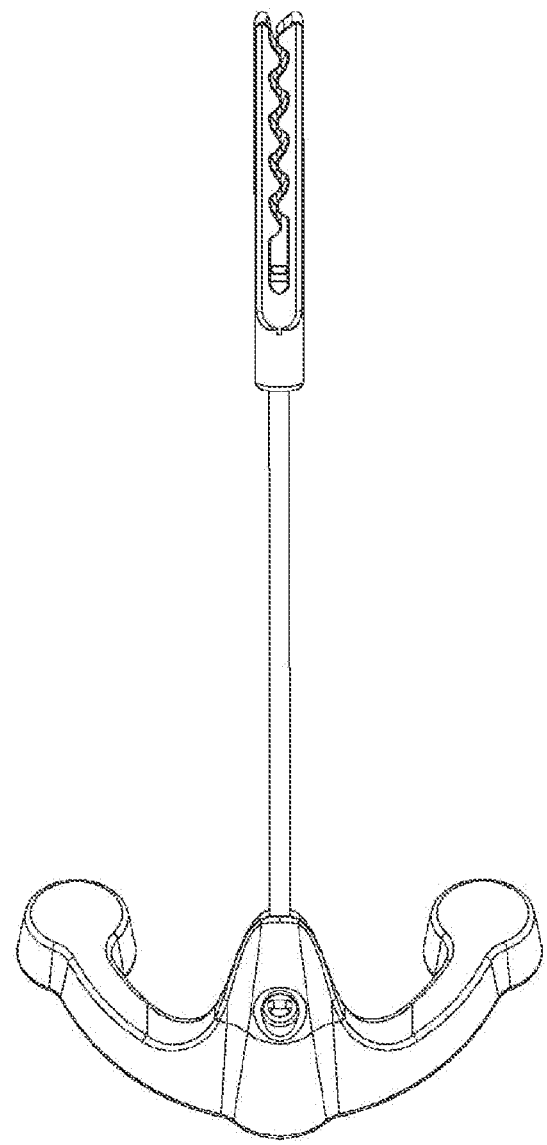
FIG. 18 shows a rear view of the device in FIG. 13.

The device 100 may be coated with a material, such as a medical grade coating material (e.g., rubber, plastic, paint, etc.), according to some implementations. FIG. 14 shows an assembled device 100 without a coating material, and FIGS. 13 and 15-18 show the assembled device with the coating material.

To use the device, for example, the practitioner orients and subcutaneously inserts the needle into the patient's skin at an incision site. Then, the base of the device is coupled to the patient's skin, and the grasper of the device is coupled to the needle. The base of the device may be coupled to the patient's skin before or after the grasper is coupled to the needle. To couple the base 102 of the device 100 to the patient's skin, the practitioner may push his or her thumb and ring finger (or other finger) against the first side 116 of the distal ends of the first 106 and second base extensions 108 to adhere the second side 118 of at least the extensions 106, 108 to the skin. A finger or part of the hand can be urged against the central base portion 104 to adhere the second side 118 of the central base portion 104 to the skin. And, the practitioner can use an intermediate finger (e.g., pointer finger) to urge the neck portion 130 and grasper 120 toward the needle. Thus, this device 100 allows for one-handed positioning of the device 100, which allows the other hand to hold the needle in position while coupling the device 100 with the needle or moving the grasper toward the needle.

In the following description, specific details are set forth describing some implementations consistent with the present disclosure. Numerous specific details are set forth to provide a thorough understanding of the implementations. It will be apparent, however, to one skilled in the art that some implementations may be practiced without some or all of these specific details. The specific implementations disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one implementations may be incorporated into other implementations unless specifically described otherwise or if the one or more features would make an implementation non-functional.

In some instances well known methods, procedures, and components have not been described in detail so as not to unnecessarily obscure aspects of the implementations.

The invention claimed is:

1. A device for supporting a medical instrument in a position, the device comprising:
   a base comprising:
      a central base portion;
      a first, elongated base extension protruding from the central base portion along at least a portion of a first axis; and
      a second, elongated base extension protruding from the central base portion along at least a portion of a second axis, the first and second axes being in a base plane that extends through the central base portion, and the first and second axes intersecting through the central base portion and being at an angle of greater than 0° and less than 180° to each other;
   a grasper for receiving a medical instrument; and
   a flexible elongated neck portion having a first end and a second end, wherein the first end is coupled with the grasper and the second end is coupled with the base, wherein a position of the first end of the flexible elongated neck portion relative to the base is adjustable,
   wherein the grasper comprises:
      a first grasper portion and a second grasper portion, the first and second grasper portions each having an inner surface and an outer surface, the inner surface and the outer surface of each of the first and second grasper portions being spaced apart and opposite each other, wherein the inner surfaces of the first and second grasper portions face each other; and
      a central grasper portion extending between the first and second grasper portions, wherein the first grasper portion extends along a first grasper axis and the second grasper portion extends along a second grasper axis, the grasper axes lying within a grasper plane that extends through the central grasper portion, and the medical instrument being receivable between the inner surfaces of the first and second grasper portions,
   wherein the inner surface of the first grasper portion comprises a first set of teeth and the inner surface of the second grasper portion comprises a second set of teeth.

2. The device of claim 1, wherein the first and second elongated base extensions are arcuate shaped as viewed in the base plane.

3. The device of claim 2, wherein the first and second elongated base extensions and the central base portion define a C-shape as viewed from the base plane.

4. The device of claim 1, wherein the first and second elongated base extensions each have proximal and distal ends, the proximal ends being coupled to the central base portion, and the distal ends of the first and second elongated base extensions are circular shaped as viewed in the base plane.

5. The device of claim 1, wherein each of the first and second elongated base extensions are flexible with respect to the central base portion and each other.

6. The device of claim 1, wherein the flexible elongated neck portion is adjustable by applying pressure to an intermediate portion of the neck portion, the intermediate portion being between the first and second ends of the neck portion.

7. The device of claim 1, wherein the grasper defines an opening, and wherein the first end of the flexible elongated neck portion is received within the grasper opening.

8. The device of claim 1, wherein the flexible elongated neck portion is integrally formed with the grasper.

9. The device of claim 1, wherein the neck portion comprises a flexible metal.

10. The device of claim 1, wherein the neck portion has a flexural rigidity of 0.003 Pa*m$^4$ to 0.4 Pa*m$^4$.

11. The device of claim 1, wherein the base has a first side and a second side, the first side being proximal to the second end of the flexible elongated neck portion and the second side being distal to the second end of the flexible elongated neck portion, at least a portion of the second side lying in a plane that is parallel to the base plane, and wherein at least a portion of the second side of the base portion comprises an adhesive coating.

12. The device of claim 11, wherein the first and second elongated base extensions each have proximal and distal ends, the proximal ends being coupled to the central base portion, and the adhesive coating is disposed on at least a portion of the second side of the distal ends of the first and second elongated base extensions.

13. The device of claim 11, wherein the adhesive coating is a gel.

14. The device of claim 1, wherein the central base portion defines an opening, and the second end of the flexible elongated neck portion is received within the base opening.

15. The device of claim 14, wherein:
the base has a first side and a second side, the first side being proximal to the second end of the flexible elongated neck portion and the second side being distal to the second end of the flexible elongated neck portion,
at least a portion of the second side of the base lying in a plane that is parallel to the base plane,
the base opening is a first base opening,
the base defines a second base opening having a central axis that is transverse to a central axis extending through the first base opening, and at least a portion of a perimeter of the second base opening is spaced apart from the second side of the base by at least 5 millimeters, and
the second end of the flexible elongated neck portion is disposed within the first opening such that the second end does not extend past the portion of the perimeter of the second base opening.

16. The device of claim 1, wherein the flexible elongated neck portion extends along a path such that the path is projected onto the base plane between the first and second axes, and the grasper is disposed past a plane that extends orthogonally through the base plane and tangentially to a distal end of each base extension.

17. The device of claim 1, wherein a contour of the first set of teeth correspond with a contour of the second set of teeth, and troughs of the first set of teeth are disposed between peaks of the second set of teeth, and vice versa.

18. The device of claim 1, wherein the first and second sets of teeth have a contour that is pitched toward the central grasper portion at an angle less than 90°, such that advancement of the medical instrument between the inner surfaces of the first and second grasper portions in a direction toward the central grasper portion produces less resistance than retraction of the medical instrument between the inner surfaces of the first and second grasper portions in a direction away from the central grasper portion.

19. The device of claim 1, wherein the inner surfaces of the first and second grasper portions comprise a frictional coating for gripping.

20. A device for supporting a medical instrument in a position, the device comprising:
a base;
a flexible elongated neck portion; and
a grasper for receiving the medical instrument, the grasper comprising:
a first grasper portion and a second grasper portion, the first and second grasper portions each having an inner surface and an outer surface, the inner surface and the outer surface of each of the first and second grasper portions being spaced apart and opposite each other, wherein the inner surfaces of the first and second grasper portions face each other, and
a central grasper portion, the first and second grasper portions extending from the central grasper portion along first and second grasper axes, respectively, wherein the grasper axes lie within a grasper plane that extends through the central grasper portion, and the medical instrument is receivable between the inner surfaces of the first and second grasper portions,
wherein the inner surface of the first grasper portion comprises a first set of teeth and the inner surface of the second grasper portion comprises a second set of teeth, and the flexible elongated neck portion extends between the base and the grasper.

21. The device of claim 20, wherein the first and second sets of teeth have a contour that is pitched toward the central grasper portion at an angle less than 90°, such that advancement of the medical instrument between the inner surfaces of the first and second grasper portions in a direction toward the central grasper portion produces less resistance than retraction of the medical instrument between the inner surfaces of the first and second grasper portions in a direction away from the central grasper portion.

* * * * *